United States Patent
Qi et al.

(10) Patent No.: US 11,931,447 B2
(45) Date of Patent: Mar. 19, 2024

(54) POLYMER/HYDROPHILIC SILICA OIL BLEND

(71) Applicants: Dow Global Technologies LLC, Midland, MI (US); Rohm and Haas Company, Collegeville, PA (US)

(72) Inventors: Luqing Qi, Midland, MI (US); Liang Chen, Sewickley, PA (US); Lu Bai, Novi, MI (US); Lyndsay M. Leal, Spring City, PA (US); David M. Meunier, Midland, MI (US); Yunshen Chen, Lexington, MA (US); Fanwen Zeng, Audubon, PA (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 346 days.

(21) Appl. No.: 17/434,440

(22) PCT Filed: Apr. 16, 2020

(86) PCT No.: PCT/US2020/028425
§ 371 (c)(1),
(2) Date: Aug. 27, 2021

(87) PCT Pub. No.: WO2020/223026
PCT Pub. Date: Nov. 5, 2020

(65) Prior Publication Data
US 2022/0142903 A1 May 12, 2022

Related U.S. Application Data

(60) Provisional application No. 62/840,486, filed on Apr. 30, 2019.

(51) Int. Cl.
| | | |
|---|---|---|
| *A61K 8/00* | (2006.01) | |
| *A61K 8/25* | (2006.01) | |
| *A61K 8/81* | (2006.01) | |
| *A61K 8/92* | (2006.01) | |
| *A61Q 5/02* | (2006.01) | |
| *A61Q 19/10* | (2006.01) | |

(52) U.S. Cl.
CPC .............. *A61K 8/8152* (2013.01); *A61K 8/25* (2013.01); *A61K 8/92* (2013.01); *A61Q 5/02* (2013.01); *A61Q 19/10* (2013.01); *A61K 2800/48* (2013.01)

(58) Field of Classification Search
CPC .................. A61K 8/8152; A61K 8/25
See application file for complete search history.

(56) References Cited

U.S. PATENT DOCUMENTS

| | | |
|---|---|---|
| 4,605,563 A | 8/1986 | Heine et al. |
| 6,261,576 B1 | 7/2001 | Fishman et al. |
| 6,906,014 B2 | 6/2005 | Haas et al. |
| 9,789,033 B2 | 10/2017 | Lu et al. |
| 2002/0034489 A1 | 3/2002 | Luchenbach et al. |
| 2005/0192190 A1 | 9/2005 | Braunagel et al. |
| 2008/0181953 A1 | 7/2008 | Cassin et al. |
| 2017/0246103 A1 | 8/2017 | Argembeaux et al. |
| 2018/0250209 A1 | 9/2018 | Chen et al. |
| 2020/0390665 A1 * | 12/2020 | El Achkar ............ A61K 8/8152 |

FOREIGN PATENT DOCUMENTS

| | | |
|---|---|---|
| EP | 561078 | 9/1993 |
| WO | 9619185 | 6/1996 |
| WO | 2017105956 | 6/2017 |
| WO | 2017105957 | 6/2017 |
| WO | 2018098038 | 5/2018 |
| WO | 2018231950 | 12/2018 |
| WO | 2018231953 | 12/2018 |
| WO | WO-2019086275 A1 * | 5/2019 ............... A61K 8/31 |

OTHER PUBLICATIONS

Search Report from corresponding Chinese Application No. 202080021739.4 dated Jul. 2, 2023.
Hasenzahl., "Fumed silica for personal care and cosmetics—versatile and effective". 2003, p. 1-8.

* cited by examiner

*Primary Examiner* — Necholus Ogden, Jr.
(74) *Attorney, Agent, or Firm* — Thomas S. Deibert

(57) ABSTRACT

A polymer/hydrophilic silica blend is provided comprising (a) a thickening polymer powder, comprising (i) structural units of $C_{4-8}$ alkyl (meth)acrylate monomer; (ii) structural units of (meth)acrylic acid monomer, and (iii) structural units of a specialized associative monomer of formula (I)

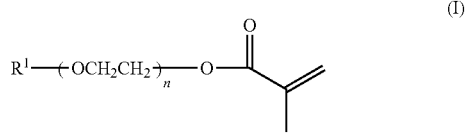

wherein $R^1$ is a linear saturated $C_{10-20}$ alkyl group; and n is an average of 20 to 28; and (b) a hydrophilic silica powder; wherein the weight ratio of hydrophilic silica powder to thickening polymer powder in the polymer/hydrophilic silica blend is 1:9 to 9:1. Also provided are personal care compositions containing same and methods of using same.

10 Claims, No Drawings

POLYMER/HYDROPHILIC SILICA OIL BLEND

The present invention relates to a polymer/hydrophilic silica blend for use in personal care applications. In particular, the present invention relates to a polymer/hydrophilic silica blend comprising: (a) a thickening polymer powder, wherein the thickening polymer powder comprises: (i) structural units of $C_{4-8}$ alkyl (meth)acrylate monomer, (ii) structural units of (meth)acrylic acid monomer; and (iii) structural units of a specialized associative monomer of formula (I), wherein $R^1$ is a linear saturated $C_{10-20}$ alkyl group; and n is an average of 20 to 28; and (b) a hydrophilic silica powder, wherein the weight ratio of hydrophilic silica powder to thickening polymer powder in the polymer/hydrophilic silica blend is 1:9 to 9:1.

Personal care compositions include a variety of additives to provide an array of benefits to the composition. One such class of additives are oil thickeners that provide viscosity enhancements and impart good aesthetics, such as good sensory feel and clarity. Oil thickening agents that are known in the art include, for example, styrene-ethylene/butadiene-styrene copolymers, polyamide polymers and cellulose based polymers. These thickeners, however, come with certain drawbacks, including insufficient viscosity enhancement, high formulation temperature and lack of consistency in viscosity control in consumer product formulations.

An approach to the oil cleanser polymer thickening compositions is disclosed in International Patent Application No. WO 2018/098038 to Chen, et al. Chen, et al. disclose a personal care composition comprising: (a) at least one cosmetically acceptable hydrophobic ester oil; (b) at least one surfactant selected from the group consisting of nonionic surfactants, anionic surfactants, and mixtures thereof; and (c) one or more polymers comprising polymerized structural units of (i) 84 to 95 weight % of $C_4$-$C_8$ (meth) acrylate monomers, (ii) 3 to 6 weight % of (meth)acrylic acid monomer, (iii) 2 to 10 weight % of lipophilically modified (meth)acrylate monomer.

Comparing to conventional oil thickeners, acrylic copolymers such as those described in Chen, et al. in International Patent Application No. WO 2018/098038 provide higher clarity in natural oils, require lower formulating temperatures and exhibit a wider compatibility with a series of natural oils and higher thickening effect. However, the thickeners as taught in Chen, et al. have been hindered due to undesirable stringiness in formulated systems.

Accordingly, there remains a need for an effective thickening system for use in oil containing personal care formulations, which thickening system imparts desirable rheology and aesthetic characteristics to the incorporating personal care formulations.

The present invention provides a polymer/hydrophilic silica blend comprising: (a) a thickening polymer powder, wherein the thickening polymer powder comprises: (i) 84 to 95 wt %, based on weight of the thickening polymer powder, of structural units of $C_{4-8}$ alkyl (meth)acrylate monomer, (ii) 0.1 to 6 wt %, based on weight of the thickening polymer powder, of structural units of (meth)acrylic acid monomer, (iii) 1 to 10, based on weight of the thickening polymer powder, of structural units of a specialized associative monomer of formula (I)

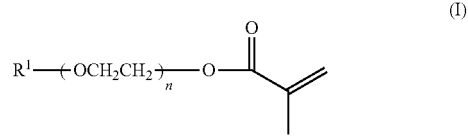

wherein $R^1$ is a linear saturated $C_{10-20}$ alkyl group; and n is an average of 20 to 28; and (b) a hydrophilic silica powder; wherein the weight ratio of hydrophilic silica powder to thickening polymer powder in the polymer/hydrophilic silica blend is 1:9 to 9:1.

The present invention provides a personal care composition, comprising: (a) a polymer/hydrophilic silica blend of the present invention; (b) a cosmetically acceptable hydrophobic ester oil, wherein the cosmetically acceptable long chain hydrophobic ester oil comprises aliphatic $C_{8-24}$ alkyl triglycerides; and (c) a cosmetically acceptable surfactant.

The present invention provides a method of treating skin or hair, comprising: providing a personal care composition of the present invention, and applying the personal care composition to at least one of skin and hair.

DETAILED DESCRIPTION

We have now surprisingly found the unique polymer/hydrophilic silica blend, as described herein, provides thickening along with a desired non-stringy aesthetic feel. Examples of personal care compositions that may benefit from the polymer oil blend of the present invention as a sensory modifier include facial care, body care, hand cream, sunscreen, deodorant, oil cleaner, body wash, shampoo and cosmetic compositions.

Unless otherwise indicated, ratios, percentages, parts, and the like are by weight.

The term "polymer" as used herein and in the appended claims refers to a compound prepared by polymerizing monomers, whether of the same or a different type. The generic term "polymer" includes the terms "homopolymer," "copolymer," and "terpolymer."

Percentages of monomer units in a polymer are percentages of solids or neat monomer weight, i.e., excluding any water present in a polymer emulsion.

The term "cosmetically acceptable" as used herein and in the appended refers to ingredients typically used in personal care compositions, and is intended to underscore that materials that are toxic when present in the amounts typically found in personal care compositions are not contemplated as part of the present invention.

The term "structural units" as used herein and in the appended claims refers to the remnant of the indicated monomer, thus a structural unit of 2-ethylhexyl acrylate is illustrated:

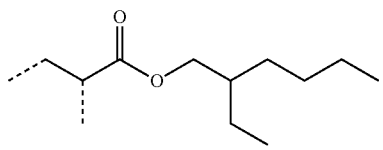

where the dotted lines represent the points of attachment to the polymer backbone.

The term "aesthetic characteristics" as used herein and in the appended claims in reference to an acidic aqueous cleansing formulation refers to visual and tactile sensory properties (e.g., smoothness, tack, lubricity, texture, color, clarity, turbidity, uniformity).

Preferably, the polymer/hydrophilic silica blend of the present invention, comprises: (a) a thickening polymer powder, wherein the thickening polymer powder comprises: (i) 84 to 95 wt % (preferably, 85 to 94 wt %; more preferably, 87.5 to 93.5 wt %; most preferably, 89.5 to 91.5), based on weight of the thickening polymer powder, of structural units of $C_{4-8}$ alkyl (meth)acrylate monomer; (ii) 0.1 to 6 wt % (preferably, 0.5 to 5 wt %; more preferably, 0.75 to 4 wt %; most preferably, 1 to 3 wt %), based on weight of the thickening polymer powder, of structural units of (meth) acrylic acid monomer, (iii) 1 to 10 (preferably, 3 to 10 wt %; more preferably, 5 to 9 wt %; most preferably, 6.5 to 8.5 wt %), based on weight of the thickening polymer powder, of structural units of a specialized associative monomer of formula (I)

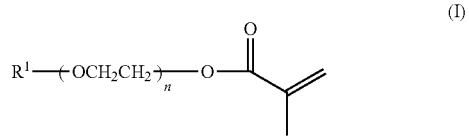

wherein $R^1$ is a linear saturated $C_{10-20}$ alkyl group (preferably, a linear saturated $C_{12-18}$ alkyl group; more preferably, a linear saturated $C_{12-14}$ alkyl group); and n is an average of 20 to 28; and (b) a hydrophilic silica powder; wherein the weight ratio of hydrophilic silica powder to thickening polymer powder in the polymer/hydrophilic silica blend is 1:9 to 9:1 (preferably, 1:4 to 4:1; more preferably, 1:3 to 3:1; still more preferably, 1:2 to 2:1; most preferably, 1:1.5 to 1.5:1).

Preferably, the polymer/hydrophilic silica blend of the present invention, comprises: a thickening polymer powder. More preferably, the polymer/hydrophilic silica blend of the present invention, comprises: 10 to 90 wt % (preferably, 20 to 80 wt %; more preferably, 25 to 75 wt %; still more preferably, 33 to 67 wt %; most preferably, 40 to 60 wt %), based on weight of the polymer/hydrophilic silica blend, of a thickening polymer powder. Most preferably, the polymer/hydrophilic silica blend of the present invention, comprises: 10 to 90 wt % (preferably, 20 to 80 wt %; more preferably, 25 to 75 wt %; still more preferably, 33 to 67 wt %; most preferably, 40 to 60 wt %), based on weight of the polymer/hydrophilic silica, of a thickening polymer powder, wherein the thickening polymer powder comprises: (i) 84 to 95 wt % (preferably, 85 to 94 wt %; more preferably, 87.5 to 93.5 wt %; most preferably, 89.5 to 91.5), based on weight of the thickening polymer powder, of structural units of $C_{4-8}$ alkyl (meth)acrylate monomer, (ii) 0.1 to 6 wt % (preferably, 0.5 to 5 wt %; more preferably, 0.75 to 4 wt %; most preferably, 1 to 3 wt %), based on weight of the thickening polymer powder, of structural units of (meth)acrylic acid monomer, and (iii) 1 to 10 (preferably, 3 to 10 wt %; more preferably, 5 to 9 wt %; most preferably, 6.5 to 8.5 wt %), based on weight of the thickening polymer powder, of structural units of a specialized associative monomer of formula (I)

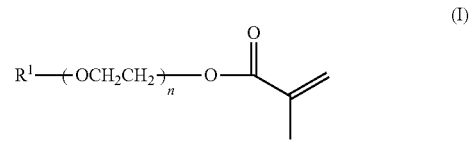

wherein $R^1$ is a linear saturated $C_{10-20}$ alkyl group; and n is an average of 2 to 60.

Preferably, the thickening polymer in emulsion, before drying into powder form, has an average particle size of 50 nm to 2 µm, as measured by a Brookhaven BI-90. More preferably, the thickening polymer in emulsion, before drying into powder form, has an average particle size of 75 nm to 1.1 µm, as measured by a Brookhaven BI-90. Most preferably, the thickening polymer in emulsion, before drying into powder form, has an average particle size of 100 to 250 nm, as measured by a Brookhaven BI-90.

Preferably, the thickening polymer powder comprises 84 to 95 wt % (preferably, 85 to 94 wt %; more preferably, 87.5 to 93.5 wt %; most preferably, 89.5 to 91.5), based on weight of the thickening polymer powder, of structural units of $C_{4-8}$ alkyl (meth)acrylate monomer. Preferably, the $C_{4-8}$ alkyl (meth)acrylate monomer is selected from the group consisting of at least one of 2-ethylhexyl (meth)acrylate, n-butyl (meth)acrylate, iso-butyl (meth)acrylate, t-butyl (meth)acrylate and mixtures thereof. More preferably, the $C_{4-8}$ alkyl (meth)acrylate monomer includes at least one of 2-ethylhexyl (meth)acrylate, n-butyl (meth)acrylate and iso-butyl (meth)acrylate. Most preferably, the $C_{4-8}$ alkyl (meth)acrylate monomer includes 2-ethylhexyl (meth)acrylate and iso-butyl (meth)acrylate).

Preferably, the thickening polymer powder comprises 79 to 95.74 wt % (preferably, 80 to 94 wt %; more preferably, 84.5 to 92 wt %; most preferably, 89.5 to 91.5), based on weight of the thickening polymer powder, of structural units of $C_{4-8}$ alkyl (meth)acrylate monomer, wherein 40 to 90 wt % (preferably, 45 to 85 wt %; more preferably, 45 to 55 wt %; still more preferably, 48 to 52 wt %; most preferably, 49 to 51 wt %) of the structural units of $C_{4-8}$ alkyl (meth)acrylate monomer are of a $C_4$ alkyl (meth)acrylate monomer, and wherein 10 to 60 wt % (preferably, 15 to 55 wt %; more preferably, 45 to 55 wt %; still more preferably, 48 to 52 wt %; most preferably, 49 to 51 wt %) of the structural units of $C_{4-8}$ alkyl (meth)acrylate monomer are of a $C_8$ alkyl (meth)acrylate monomer. More preferably, the thickening polymer powder comprises 79 to 95.74 wt % (preferably, 80 to 94 wt %; more preferably, 84.5 to 92 wt %; most preferably, 89.5 to 91.5), based on weight of the thickening polymer powder, of structural units of $C_{4-8}$ alkyl (meth)acrylate monomer; wherein 40 to 90 wt % (preferably, 45 to 85 wt %; more preferably, 45 to 55 wt %; still more preferably, 48 to 52 wt %; most preferably, 49 to 51 wt %) of the structural units of a $C_{4-8}$ alkyl (meth)acrylate monomer are of iso-butyl methacrylate; and wherein 10 to 60 wt % (preferably, 15 to 55 wt %; more preferably, 45 to 55 wt %; still more preferably, 48 to 52 wt %; most preferably, 49 to 51 wt %) of the structural units of $C_{4-8}$ alkyl (meth)acrylate monomer are of 2-ethylhexyl methacrylate.

Preferably, the thickening polymer powder comprises 0.1 to 6 wt % (preferably, 0.5 to 5 wt %; more preferably, 0.75 to 4 wt %; most preferably, 1 to 3 wt %), based on weight of the thickening polymer powder, of structural units of (meth)acrylic acid monomer. More preferably, the thickening polymer powder comprises 0.1 to 6 wt % (preferably, 0.5 to 5 wt %; more preferably, 0.75 to 4 wt %; most preferably, 1 to 3 wt %), based on weight of the thickening polymer powder, of structural units of methacrylic acid monomer.

Preferably, the thickening polymer powder comprises 1 to 10 (preferably, 3 to 10 wt %; more preferably, 5 to 9 wt %; most preferably, 6.5 to 8.5 wt %), based on weight of the thickening polymer powder, of structural units of a specialized associative monomer of formula (I), wherein $R^1$ is a linear saturated $C_{10\text{-}20}$ alkyl group (preferably, a linear saturated $C_{12\text{-}18}$ alkyl group; more preferably, a linear saturated $C_{12\text{-}14}$ alkyl group); and n is an average of 2 to 60 (preferably, 5 to 40; more preferably, 10 to 35; most preferably, 20 to 28).

Preferably, the thickening polymer powder contains<1 wt %, based on weight of the thickening polymer, of structural units of (methoxy) poly(ethylene glycol) monomer. As used herein and in the appended claims, the term "(methoxy) poly(ethylene glycol) (meth)acrylate" means methoxy poly (ethylene glycol) methacrylate, methoxy poly(ethylene glycol) acrylate, poly(ethylene glycol) methacrylate and poly (ethylene glycol) acrylate. More preferably, the thickening polymer powder contains<1 wt % (preferably, <0.1 wt %; more preferably, <0.001 wt %; most preferably, <detectable limit), based on weight of the thickening polymer, of structural units of methoxy poly(ethylene glycol) methacrylate, methoxy poly(ethylene glycol) acrylate, poly(ethylene glycol) methacrylate and poly(ethylene glycol) acrylate. Most preferably, the thickening polymer powder contains<1 wt % (preferably, <0.1 wt %; more preferably, <0.001 wt %; most preferably, <detectable limit), based on weight of the thickening polymer, of structural units of methoxy poly(ethylene glycol) methacrylate, methoxy poly(ethylene glycol) acrylate, poly(ethylene glycol) methacrylate and poly(ethylene glycol) acrylate, collectively.

Preferably, the thickening polymer powder is provided using at least one of spray drying, freeze drying and coagulation. More preferably, the thickening polymer powder is spray dried. In certain spray drying processes, anti-caking agents may be mixed with an acrylic polymer suspension prior to spray drying or introduced as a dry powder during the spray drying process. Anti-caking agents include mineral fillers (e.g., calcium carbonate, kaolin, titanium oxide, talc, hydrated alumina, bentonite and silica); solid polymer particles with a glass transition or melting temperature above 60° C. (e.g., polymethylmethacrylate, polystyrene and high density polyethylene); and water soluble polymers with a glass transition temperature above 60° C. (e.g., polyvinyl alcohol and methylcellulose). The anti-caking agents are used as flow aids to help prevent the dried polymer particles from sticking to each other or the processing equipment. Anti-caking agents may be included in the processing at up to 20 wt %, based on the weight of the collected polymer powder. Note that thickening polymer powder produced using silica as a flow aid surprisingly does not exhibit the same superior performance associated with physical blending of silica powder and thickening polymer powder in the invention as described and claimed herein.

Preferably, the polymer/hydrophilic silica blend of the present invention, comprises: a hydrophilic silica powder. More preferably, the polymer/hydrophilic silica blend of the present invention, comprises: 10 to 90 wt % (preferably, 20 to 80 wt %; more preferably, 25 to 75 wt %; still more preferably, 33 to 67 wt %; most preferably, 40 to 60 wt %), based on weight of the polymer/hydrophilic silica blend, of a hydrophilic silica powder. Most preferably, the polymer/ hydrophilic silica blend of the present invention, comprises: 10 to 90 wt % (preferably, 20 to 80 wt %; more preferably, 25 to 75 wt %; still more preferably, 33 to 67 wt %; most preferably, 40 to 60 wt %), based on weight of the polymer/ hydrophilic silica blend, of a hydrophilic silica powder, wherein the hydrophilic silica powder is a fumed hydrophilic silica powder.

In preparing the polymer/hydrophilic silica blend of the present invention, the thickening polymer powder and the silica powder are mixed as dry solids (i.e., wherein the thickening polymer is isolated in dry powder form before it is combined with the silica powder to form the polymer oil blend).

Preferably, the personal care composition of the present invention, comprises: (a) a polymer/hydrophilic silica blend of the present invention; (b) a cosmetically acceptable hydrophobic ester oil, wherein the cosmetically acceptable hydrophobic ester oil comprises an aliphatic $C_{8\text{-}24}$ alkyl triglyceride (preferably, an aliphatic $C_{12\text{-}24}$ alkyl triglyceride; more preferably, an aliphatic $C_{>12\text{-}24}$ alkyl triglyderide); and (c) a cosmetically acceptable surfactant. More preferably, the personal care composition of the present invention, comprises: (a) 1 to 10 wt % (preferably, 2 to 8 wt %; more preferably, 4 to 6 wt %; most preferably, 4.5 to 5.5), based on weight of the personal care composition, of a polymer/ hydrophilic silica blend of the present invention; (b) 40 to 75 wt % (preferably, 45 to 70 wt %; more preferably, 55 to 60 wt %; most preferably, 56 to 58 wt %), based on weight of the personal care composition, of a cosmetically acceptable hydrophobic ester oil, wherein the cosmetically acceptable hydrophobic ester oil comprises an aliphatic $C_{8\text{-}24}$ alkyl triglyceride (preferably, an aliphatic $C_{12\text{-}24}$ alkyl triglyceride; more preferably, an aliphatic $C_{>12\text{-}24}$ alkyl triglyderide); and (c) 15 to 59 wt % (preferably, 20 to 53 wt %; more preferably, 34 to 41 wt %; most preferably, 36 to 40 wt %), based on weight of the personal care composition, of a cosmetically acceptable surfactant.

Preferably, the personal care composition of the present invention, comprises: a cosmetically acceptable hydrophobic ester oil. More preferably, the personal care composition of the present invention, comprises: a cosmetically acceptable hydrophobic ester oil, wherein the cosmetically acceptable hydrophobic ester oil comprises an aliphatic $C_{8\text{-}24}$ alkyl triglyceride (preferably, an aliphatic $C_{12\text{-}24}$ alkyl triglyceride; more preferably, an aliphatic $C_{>12\text{-}24}$ alkyl triglyderide). Still more preferably, the personal care composition of the present invention, comprises: 40 to 75 wt % (preferably, 45 to 70 wt %; more preferably, 55 to 60 wt %; most preferably, 56 to 58 wt %), based on weight of the personal care composition, of a cosmetically acceptable hydrophobic ester oil, wherein the cosmetically acceptable hydrophobic ester oil comprises an aliphatic $C_{8\text{-}24}$ alkyl triglyceride (preferably, an aliphatic $C_{12\text{-}24}$ alkyl triglyceride; more preferably, an aliphatic $C_{>12\text{-}24}$ alkyl triglyderide). Still yet more preferably, the personal care composition of the present invention, comprises: 40 to 75 wt % (preferably, 45 to 70 wt %; more preferably, 55 to 60 wt %; most preferably, 56 to 58 wt %), based on weight of the personal care composition, of a cosmetically acceptable hydrophobic ester oil, wherein the cosmetically acceptable hydrophobic ester oil is selected from the group consisting of caprylic/capric triglycerides; saturated fatty esters and diesters (e.g., isopropyl palmitate, octyl palmitate, butyl stearate, isocetyl stearate, octadodecyl stearate, octadodecyl stearoyl stearate, diisopropyl adipate and dioctyl sebacate); animal oils (e.g., mink oil) and vegetable oils. Most preferably, the personal care composition of the present invention, comprises: 40 to 75 wt % (preferably, 45 to 70 wt %; more preferably, 55 to 60 wt %; most preferably, 56 to 58 wt %), based on weight of the personal care composition, of a cosmetically acceptable hydrophobic ester oil, wherein the cosmetically acceptable hydrophobic ester oil is selected from the group consisting of almond oil, andiroba oil, apricot kernel oil, argan oil, avacado oil, babassu oil, borage oil, canola oil, castor oil, coca butter, coconut oil, corn oil, cottonseed oil, crambe oil, cupuacu butter, evening primrose, grape seed oil, hazelnut oil, hybrid safflower oil, illipe butter, Japan wax, jatropha oil, jojoba oil, kokhum butter, linseed oil, mango butter, meadowfoam oil, milk fat, olive oil, ongokea oil, palm kernel oil, palm oil, peanut oil, poppyseed oil, rapeseed oil, rice bran oil, safflower oil, sesame oil, shea butter, soybean oil, sunflower oil, sweet almond oil, tallow, tung oil, walnut oil, wheat germ oil, veronia oil and mixtures thereof (preferably, corn oil, cotton seed oil, soybean oil, sunflower oil and mixtures thereof; more preferably, corn oil, sunflower oil and mixtures thereof; most preferably, sunflower oil).

Preferably, the personal care composition of the present invention further comprises a cosmetically acceptable surfactant. More preferably, the personal care composition of the present invention further comprises a cosmetically acceptable surfactant selected from the group consisting of anionic surfactants, nonionic surfactants, zwitterionic surfactants and mixtures thereof. Most preferably, the personal care composition of the present invention further comprises a cosmetically acceptable surfactant selected from the group consisting of anionic surfactants, nonionic surfactants and mixtures thereof.

Preferably, the personal care composition of the present invention, comprises a cosmetically acceptable surfactant. More preferably, the personal care composition of the present invention comprises 15 to 59 wt % (preferably, 20 to 53 wt %; more preferably, 34 to 41 wt %; most preferably, 36 to 40 wt %), based on weight of the personal care composition, of a cosmetically acceptable surfactant selected from the group consisting of anionic surfactants, nonionic surfactants, zwitterionic surfactants and mixtures thereof. Most preferably, the personal care composition of the present invention comprises 15 to 59 wt % (preferably, 20 to 53 wt %; more preferably, 34 to 41 wt %; most preferably, 36 to 40 wt %), based on weight of the personal care composition, of a cosmetically acceptable surfactant, wherein the cosmetically acceptable surfactant is a mixture of an anionic surfactant, a nonionic surfactant and a zwitterionic surfactant.

Preferably, the anionic surfactants used in the personal care composition of the present invention are selected from the group of cosmetically acceptable anionic surfactants. Preferably, the cosmetically acceptable anionic surfactants are selected from the group consisting of alkyl sulfates; alkyl ether sulfates; alkyl ether carboxylates; alkyl-substituted aryl sulfonates; alkyl succinates; alkyl sulfosuccinates; alkyl sarcosinates; α-olefin sulfonates; sodium, magnesium, ammonium, ethanolamine, diethanolamine and triethanolamine salts thereof; and mixtures thereof.

Preferred alkyl ether sulfate surfactants include ammonium capryleth sulfate, ammonium $C_{12-15}$ pareth sulfate, ammonium laureth sulfate, ammonium laureth-5 sulfate, ammonium myreth sulfate, diethanol amine $C_{12-13}$ pareth-3 sulfate, diethanol amine laureth sulfate, diethanol amine myreth sulfate, diethylamine laureth sulfate, magnesium coceth sulfate, magnesium laureth sulfate, magnesium laureth-5 sulfate, magnesium myreth sulfate, magnesium oleth sulfate, monoethanol amine laureth sulfate, monoisopropanolamine $C_{12-15}$ pareth sulfate, monoisopropanolamine laureth sulfate, sodium coceth sulfate, sodium $C_{9-15}$ pareth-3 sulfate, sodium $C_{10-15}$ pareth-3 sulfate, sodium $C_{12-16}$ pareth-2 sulfate, sodium $C_{12-13}$ pareth sulfate, sodium $C_{12-14}$ pareth-3 sulfate, sodium $C_{12-15}$ pareth sulfate, sodium $C_{12-15}$ pareth-3 sulfate, sodium $C_{13-15}$ pareth-3 sulfate, sodium doceth sulfate, sodium laneth sulfate, sodium laureth sulfate, sodium laureth-5 sulfate, sodium myreth sulfate, sodium oleth sulfate, triethanolamine laureth sulfate, triethanolamine laneth sulfate and triisopropanolamine laureth sulfate.

Preferably, the nonionic surfactants used in the personal care composition of the present invention are selected from the group of cosmetically acceptable nonionic surfactants. Preferably, the cosmetically acceptable nonionic surfactants include long-chain fatty acid mono- and di-alkanolamides (e.g., behenoyl monoethanolamide, coco monoethanolamide, isostearoyl monoethanolamide, lauroyl monoethanolamide, myristoyl monoethanolamide, oleoyl monoethanolamide, ricinoleoyl monoethanolamide, stearoyl monoethanolamide, behenoyl diethanolamide, caproyl diethanolamide, cocoyl diethanolamide, isostearoyl diethanolamide, lauroyl diethanolamide, lineloyl monoethanolamide, myristoyl monoethanolamide, oleoyl monoethanolamide, palmitoyl diethanolamide, ricinoleoyl monoethanolamide and stearoyl monoethanolamide); $C_{12-22}$ fatty alcohol ethoxylates (e.g., oleth-2, oleth-3, oleth-4, oleth-5, oleth-6, oleth-7, oleth-8, oleth-9, oleth-10, oleth-11, oleth-12, oleth-15, oleth-16, oleth-20, oleth-25, laureth-2, laureth-3, laureth-4, laureth-5, laureth-6, laureth-7, laureth-8, laureth-9, laureth-10, laureth-11, laureth-12, laureth-13, laureth-15, laureth-16, laureth-20, laureth-25, ceteth-10, ceteth-12, ceteth-14, ceteth-15, ceteth 16, ceteth-17, ceteth-20, ceteth-25, cetoleth-10, cetoleth-12, cetoleth-14, cetoleth-15, cetoleth-16, cetoleth-17, cetoleth-20, cetoleth-25, ceteareth-10, ceteareth-12, ceteareth-14, ceteareth-15, ceteareth-16, ceteareth-18, ceteareth-20, ceteareth-22, ceteareth-25, isosteareth-10, isosteareth-12, isosteareth-15, isosteareth-20, isosteareth-22, isosteareth-25, steareth-10, steareth-11, steareth-14, steareth-15, steareth-16, steareth-20 and steareth-25); alkyl polyglucosides (e.g., decyl glucoside, carpylyl glucoside, ceteary glucoside, cocoyl ethyl glucoside, lauryl glucoside, myristyl glucoside and cocoglucoside); polyalkylene glycol ethers of fatty acid glyceride or partial glyceride (e.g., PEG-30 hydrogenated castor oil, PEG-35 hydrogenated castor oil, PEG-40 hydrogenated castor oil, PEG-45 hydrogenated castor oil, PEG-50 hydrogenated castor oil, PEG-55 hydrogenated castor oil, PEG-60 hydrogenated castor oil, PEG-65 hydrogenated castor oil, PEG-80 hydrogenated castor oil, PEG-100 hydrogenated castor oil, PEG-200 hydrogenated castor oil, PEG-35 castor oil, PEG-50 castor oil, PEG-55 castor oil, PEG-60 castor oil, PEG-80 castor oil and PEG-100 castor oil) and mixtures thereof. More preferably, the cosmetically acceptable nonionic surfactant includes Laureth-4. Most preferably, the cosmetically acceptable nonionic surfactant is Laureth-5.

Preferably, the zwitterionic surfactants used in the personal care composition of the present invention are selected from the group of cosmetically acceptable zwitterionic surfactants. Preferably, the cosmetically acceptable zwitterionic surfactants are selected from the group consisting of alkyl amine oxides, alkyl betaines, alkyl amido propyl betaines, alkyl alkanol amides, alkyl di-alkanol amides, alkyl sulfobetaines, alkyl glycinates, alkyl carboxy glycinates and mixtures thereof. More preferably, the cosmetically acceptable zwitterionic surfactants are selected from the group consisting of $C_{8-18}$ alkyl amine oxides, $C_{8-18}$ alkyl betaines, $C_{8-18}$ alkyl amido propyl betaines, $C_{8-18}$ alkyl alkanol amides, $C_{8-18}$ alkyl di-alkanol amides, $C_{8-18}$ alkyl sulfobetaines, $C_{8-18}$ alkyl glycinates, $C_{8-18}$ alkyl carboxy glycinates and mixtures thereof. Preferred cosmetically acceptable zwitterionic surfactants include lauryl amine oxide, cocamide monoethanolamine, cocamide diethanolamine, cocamidopropyl betaine, cocodimethyl sulfopropyl betaine and mixtures thereof. Most preferred cosmetically acceptable zwitterionic surfactants include cocamide diethanolamine.

Preferably, the personal care composition of the present invention may optionally further comprise at least one personal care additive selected from the group consisting of abrasives; absorbents; fragrances; pigments; colorings/colorants; essential oils; skin sensates; astringents (e.g., clove oil, menthol, camphor, eucalyptus oil, eugenol, menthyl lactate, witch hazel distillate); preservatives; anti-caking agents; foam builders; antifoaming agents; antimicrobial agents (e.g., iodopropyl butylcarbamate); antioxidants; binders; biological additives; buffering agents; bulking agents; chelating agents; chemical additives; cosmetic astringents; cosmetic biocides; denaturants; drug astringents; topical analgesics; film formers; opacifying agents; pH adjusters; propellants; reducing agents; sequestrants; skin bleaching and lightening agents (e.g., hydroquinone, kojic acid, ascorbic acid, magnesium ascorbyl phosphate, ascorbyl glucosamine); skin conditioning agents (e.g., hymectants); skin soothing agents (e.g., panthenol, aloe vera, pantothenic acid, allantoin, bisabolol, dipotassium glycyrrhizinate); skin treating agents; vitamins (e.g., Vitamin C); silicones and fatty alcohols.

Preferably, the method of treating skin or hair of the present invention, comprises: providing a personal care composition of the present invention and applying the personal care composition to at least one of a skin and hair. More preferably, the method of using a personal care composition of the present invention, further comprises: rinsing the personal care composition from the at least one of skin and hair with a rinse water.

Some embodiments of the present invention will now be described in detail in the following Examples.

Example S1: Synthesis of Polymer 1

A thickening polymer having the structural units of monomer content noted in TABLE 1 was prepared in a three liter round bottom flask equipped with a mechanical overhead stirrer, a heating mantle, a thermocouple, a condenser and inlets for the addition of monomer, initiator and nitrogen. To the flask was charged deionized water (900 g) and sodium dodecylbenzene sulfonate (7.46 g; DS-4 Polystep A-16-22 from Stepan). The flask contents were then set to stir with a nitrogen flow and heated to 87-89° C. In a separate plastic lined vessel with overhead stirring was added sodium dodecylbenzene sulfonate (17.68 g) and deionized water (256.65 g) and mixed. To the vessel contents was then added a lipophilically modified monomer (LIPO) having the following structure

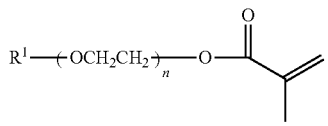

wherein $R^1$ is a linear saturated $C_{12}$ alkyl group and wherein n is an average of 20 to 28 (60.60 g), isobutyl methacrylate (255.93 g), 2-ethylhexyl methacrylate (255.93 g) and methacrylic acid (11.31 g) with continued mixing to form a smooth, stable monomer emulsion. An initial catalyst charge of ammonium persulfate (0.28 g) in deionized water (12.71 g) was prepared and set aside. A buffer solution of ammonium bicarbonate (1.92 g) in deionized water (12.71 g) was prepared and set aside. A preform seed of 22.38 grams was removed from the stable monomer emulsion and put into a small beaker. A rinse of deionized water (16.8 g) was prepared. A co-feed catalyst charge of ammonium persulfate (0.28 g) in deionized water (49.22 g) was prepared and set aside.

When the contents of the flask was at temperature, the buffer solution and initial catalyst charge were added to the flask contents, followed by addition of the preform seed and rinse. The reaction was monitored for a small exotherm. After the exotherm, the temperature control was adjusted to 83-85° C. The monomer emulsion was then added to the flask, sub-surface, at a rate of 5.25 g/min. for 15 minutes after which the rate was increased to 10.5 g/min. for 75 minutes. While the monomer emulsion was added to the flask, the co-feed catalyst solution was simultaneously added at a rate of 0.55 g/min. Upon completion of the monomer emulsion and co-feed catalyst additions, deionized water (16.8 g) was added as a rinse. The contents of the flask were then held for 20 minutes at 83-85° C.

During the hold, a chase promoter of 3.77 grams of a 0.15% iron sulfate heptahydrate solution was prepared. A chase activator solution of isoascorbic acid (1.12 g) dissolved in deionized water (36.40 g) was prepared. A chase catalyst solution of 70% tert-butyl hydroperoxide (2.14 g) in deionized water (35.40 g) was prepared.

At 80° C., the chase promoter solution was added as a shot to the flask. The flask contents were then cooled to 70° C., while adding the chase activator and chase catalyst solutions separately by syringe over 60 minutes at a feed rate of 0.7 g/min. The flask contents were then held for 10 minutes, and then cooled to room temperature. When the flask contents reached room temperature, the emulsion product was filtered through a 100 mesh bag.

The filtered emulsion product was then spray dried using a two-fluid nozzle atomizer equipped on a Mobile Minor spray dryer (GEA Process Engineering Inc.). The spray drying was performed under an inert nitrogen atmosphere. Nitrogen was supplied to the atomizer at ambient temperature, 1 bar and a 6.0 kg/hour flow rate. The polymer emulsion was fed into the atomizer at 30 mL/min using a peristaltic pump (Masterflex US). Heated nitrogen was used to evaporate the water. The inlet temperature was set at 140° C., and the outlet temperature was equilibrated at 40-50° C. by fine tuning the emulsion feed rate. The resulting polymer powder was collected in a glass jar attached to the cyclone and subsequently vacuum dried at room temperature to remove residual moisture.

TABLE 1

| Sample | Structural units of monomer (wt %) | | | |
|---|---|---|---|---|
| | iBMA | EHMA | MAA | LIPO |
| Polymer 1 | 45.25 | 45.25 | 2 | 7.5 | iBMA = isobutyl methacrylate
EHMA = 2-ethylhexyl methacrylate
MAA = methacrylic acid
LIPO = specialized associated monomer of formula (I), wherein $R^1$ is a linear saturated $C_{12}$ alkyl group and n is an average of 20 to 28

Comparative Examples C1-C2 and Example 1: Oil Cleanser Formulations

Oil cleanser formulations were prepared having the compositions noted in TABLE 2, by mixing through an overhead mixer first under room temperature at 750 rpm for 15 minutes, followed by another 15 minute mixing at 60° C. at 500 rpm. Heating was applied only after the polymer and silica were fully mixed into the oil.

Stringiness Evaluation

The stringiness of the oil cleanser formulations of Comparative Examples C1-C2 and Example 1 was evaluated using a Thermo Haake Capillary Break-up Extensional Rheometer (CaBER) with 6 mm diameter parallel plates at ambient conditions. The initial gat was set at 3 mm and the stretch profile was set at 50 ms linear strike. The filament diameter was recorded as a function of time by the instrument using an infrared laser micrometer. Time zero was set at the moment when the upper plate started moving. All samples were tested in duplicate with the average reported in TABLE 2.

TABLE 2

| Ex. | Polymer S1 (wt %) | Silica[1] (wt %) | Oil/Surf[2] (wt %) | Filament Break-up Time (s) |
|---|---|---|---|---|
| C1 | 5 | — | 95 | 6.12 |
| C2 | — | 5 | 95 | 0.15 |
| 1 | 2.5 | 2.5 | 95 | 0.065 |

[1]Aerosil 200 hydrophilic fumed silica available from Evonik.
[2]A mixture of (a) 60 wt % sunflower seed oil available from Spectrum Chemical, (b) 30 wt % Lumorol ® K1000 a surfactant blend of 60 wt % MIPA-laureth sulfate, 30 wt % Laureth-4 and 10 wt % cocamide DEA available from Integrated Chemicals Specialties BV and (c) 10 wt % Rhoedol 430 V polyoxyethylene sorbitol tetraoleate available from Kao Global Chemicals.

We claim:

1. A polymer/hydrophilic silica blend comprising:
   (a) a thickening polymer powder, wherein the thickening polymer powder comprises:
      (i) 84 to 95 wt %, based on weight of the thickening polymer powder, of structural units of $C_{4-8}$ alkyl (meth)acrylate monomer;
      (ii) 0.1 to 6 wt %, based on weight of the thickening polymer powder, of structural units of (meth)acrylic acid monomer, and
      (iii) 1 to 10, based on weight of the thickening polymer powder, of structural units of a specialized associative monomer of formula (I)

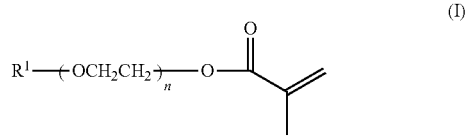

wherein $R^1$ is a linear saturated $C_{10-20}$ alkyl group; and n is an average of 20 to 28; and
   (b) a hydrophilic silica powder;
   wherein the weight ratio of hydrophilic silica powder to thickening polymer powder in the polymer/hydrophilic silica blend is 1:9 to 9:1.

2. A personal care composition, comprising:
   (a) a polymer/hydrophilic silica blend according to claim 1;
   (b) a cosmetically acceptable hydrophobic ester oil, wherein the cosmetically acceptable long chain hydrophobic ester oil comprises aliphatic $C_{8-24}$ alkyl triglycerides; and
   (c) a cosmetically acceptable surfactant.

3. The personal care composition of claim 2, wherein the cosmetically acceptable hydrophobic ester oil is selected from the group consisting of almond oil, andiroba oil, apricot kernel oil, argan oil, avacado oil, babassu oil, borage oil, canola oil, castor oil, coca butter, coconut oil, corn oil, cottonseed oil, crambe oil, cupuacu butter, evening primrose, grape seed oil, hazelnut oil, hybrid safflower oil, illipe butter, Japan wax, jatropha oil, jojoba oil, kokhum butter, linseed oil, mango butter, meadowfoam oil, milk fat, olive oil, ongokea oil, palm kernel oil, palm oil, peanut oil, poppyseed oil, rapeseed oil, rice bran oil, safflower oil, sesame oil, shea butter, soybean oil, sunflower oil, sweet almond oil, tallow, tung oil, walnut oil, wheat germ oil, veronia oil and mixtures thereof.

4. The personal care composition of claim 2, wherein the $C_{4-8}$ alkyl (meth)acrylate monomer is selected from the group consisting of at least one of ethylhexyl (meth)acrylate, n-butyl (meth)acrylate, iso-butyl (meth)acrylate and t-butyl (meth)acrylate.

5. The personal care composition of claim 2, wherein 40 to 90 wt % of the structural units of $C_{4-8}$ alkyl (meth)acrylate monomer are derived from a $C_4$ alkyl (meth)acrylate monomer and wherein 10 to 60 wt % are derived from a $C_8$ (meth)acrylate monomer.

6. The personal care composition of claim 5, wherein the $C_4$ alkyl (meth)acrylate monomer is iso-butyl methacrylate and the $C_8$ alkyl (meth)acrylate is ethylhexyl methacrylate.

7. The personal care composition of claim 2, wherein the thickening polymer comprises 3 to 10 wt %, based on weight of the thickening polymer powder, of structural units of the specialized associative monomer of formula (I), wherein $R^1$ is a linear saturated $C_{12-18}$ alkyl group.

8. The personal care composition of claim 2, further comprising an additive selected from the group consisting of abrasives, absorbents, fragrances, pigments, colorings/colorants, essential oils, skin sensates, astringents, preservatives, anti-caking agents, foam builders, antifoaming agents, antimicrobial agents, antioxidants, binders, biological additives, buffering agents, bulking agents, chelating agents, chemical additives, cosmetic astringents, cosmetic biocides, denaturants, drug astringents, external analgesics, film formers, opacifying agents, pH adjusters, propellants, reducing agents, sequestrants, skin bleaching and lightening agents, skin conditioning agents, skin soothing agents, skin treating agents, vitamins, silicones, fatty alcohols and mixtures thereof.

9. The personal care composition of claim 2, wherein the cosmetically acceptable surfactant comprises a blend of anionic surfactants and non-ionic surfactants.

10. A method of treating skin or hair, comprising:
    providing a personal care composition according to claim 2, and
    applying the personal care composition to at least one of skin and hair.

* * * * *